(12) United States Patent
Nicklin et al.

(10) Patent No.: US 6,274,368 B1
(45) Date of Patent: Aug. 14, 2001

(54) BIODEGRADATION OF EXPLOSIVES

(75) Inventors: Stephen Nicklin, Farnborough; Christopher Edward French, Edinburgh; Neil Charles Bruce, Cambridge; Emma Rachel Travis, Cambridge; Amrik Basran, Cambridge, all of (GB)

(73) Assignee: The Secretary of State for Defence in Her Britannic Majesty's Government of the United Kingdom of Great Britain and Northern Ireland, Hants (GB)

( * ) Notice: Subject to any disclaimer, the term of this patent is extended or adjusted under 35 U.S.C. 154(b) by 0 days.

(21) Appl. No.: 09/202,933
(22) PCT Filed: Aug. 21, 1997
(86) PCT No.: PCT/GB97/02242
§ 371 Date: Dec. 23, 1998
§ 102(e) Date: Dec. 23, 1998
(87) PCT Pub. No.: WO98/07839
PCT Pub. Date: Feb. 26, 1998

(30) Foreign Application Priority Data

Aug. 21, 1996 (GB) .................................................. 9617537

(51) Int. Cl.[7] .............................. B09B 3/00; C12N 1/00; C12N 1/20; C12P 21/04; C12Q 1/02

(52) U.S. Cl. ...................... 435/252.1; 435/29; 435/71.1; 435/262.5; 435/822

(58) Field of Search ..................................... 435/29, 252.1, 435/262, 822, 71.1, 262.5

(56) References Cited

PUBLICATIONS

Jones et al., XP 002047832 Biodegradability of Selected Highly Energetic Pollutants Under Aerobic Conditions, pp. 251–257 (1995).
Travis et al., XP 002047834 O–10. Biodegradation of the Explosive Hexahydro–1,3,5–trinitro–1,3,5–triazine by *Rhodococcus rhodochrous* strain 11Y, 1 page (1997).

*Primary Examiner*—Deborah K. Ware
(74) *Attorney, Agent, or Firm*—Nixon & Vanderhye

(57) ABSTRACT

An enzymically active cell free extract or membrane fraction capable of catalysing the removal of nitrite from hexahydro-1,3,5-trinitro-1,3,5-triazine (RDX) is provided. The cell free extract is produced by culturing a strain of *Rhodococcus rhodochrous* bacterium from nature. The strain designated 11Y has been deposited as NCIMB 40820. Methods of bioremediation using the enzymically active cell free extract so produced are also provided. Additionally there is provided a method for detecting the presence of RDX in a sample together with a biosensor for use in such a method. The nitrite produced in the enzyme catalysed reaction with RDX is detected, for example, colorimetrically, or alternatively a product of RDX degradation, such as formalbehyde, is detected.

13 Claims, 4 Drawing Sheets

BIODEGRADATION OF EXPLOSIVES

This invention relates to the field of explosives detection and biodegradation and in particular to novel bacterial isolate and a novel enzymic activity, i.e. a single enzyme or group of enzymes, derived therefrom. This invention further relates to the aerobic biodegradation of hexahydro-1,3,5-trinitro-1,3,5-triazine (hereinafter referred to by the commonly used abbreviation RDX) and to methods and apparatus for the detection of RDX using the RDX degrading enzymic activity.

The novel enzymic activity has been shown to liberate nitrite from RDX, a heterocyclic nitramine.

Nitramines, although apparently extremely rare in nature, are produced in significant quanties by the chemical industry and comprise, for example, an important class of energetic materials having applications as explosives and propellants, RDX is currently the most important mlitary explosive in the United States. The manufacture, handling and disposal of RDX can all lead to the contamination of the environment with RDX. There are concerns regarding the environmental fate of nitramines due to their relative recalcitrance and therefore there exists a need for a means of removing such contaminants from the environment without producing other undesirable pollutants. There is also an urgent requirement for a better method of detecting RDX as the currently proposed analytical systems rely mostly on bulky and sophisticated pieces of equipment such as High Performance Liquid Chromatography and/or require specially trained laboratory technicians for their application.

It is an aim of this invention to provide an enzyme which is capable of catalysing the biodegradation of RDX and which may be employed in a bioremediation system for the environmental contamination of the RDX pollutant. It is a further aim of this project to provide an enzyme which is useful for RDX detection systems.

Thus according to a first aspect of the invention there is provided a *Rhodococcus rhodochrous* 11Y bacterial strain preferred to as "11Y" and deposited as NCIMB 40820, and mutants and variants thereof, capable of producing enzymic activity which degrades hexahydro-1,3,5-trinitro-1,3,5-triazine (RDX) and in a second aspect of the invention there is provided an RDX degrading enzymic activity characterised in that it catalyses the release of nitrite from hexahydro-1,3,5-trinitro-1,3,5-triazine (RDX) and is obtained from cells of *Rhodacoccus rhodochrous* 11Y or mutants or variants thereof.

This enzymic activity shows lesser activity against the similar heterocyclic nitramine octahydro-1,3,5,7-tetranitro-1,3,5,7-tetrazocine (HMX) and less activity again against the nitrate ester pentaerythritol tetranitrate (PETN). The activity was found to be membrane-associated and could be solubilised from the membrane with 5% triton. There is no requirement for a co-factor such as NADPH, NADH, PES or FAD for enzymic activity and the enzymic activity exhibits stablilty to the presence of relatively high concentrations of denaturants and the activity is increased in the presence of urea. The enzymic activity is also relatively stable to heat denaturation. Further, a large proportion of the enzymic activity remains soluble when the pH is reduced to 3.5 with glacial acetic acid.

The bacterial strain from which the enzymic activity of the current invention is obtained was isolated from nutur and is a strain of *Rhodococcus rhodochrous* herein designated 11Y. A sample of the novel isolate has been deposited under the terms of the Budapest Treaty on the International Recognition of the Deposit of Microorganisms for the purpose of patent procedure at the UK National Collection of Industrial and Marine Bacteria, 23 St. Machar Drive, Aberdeen, AB2 1RY, Scotland on Aug. 7, 1996 under the deposit number NCIMB 40820.

| Gram stain | +ve |
| Spores | −ve |
| Motility | −ve |
| Growth | |
| 37° C. | +ve |
| 41° C. | +ve |
| 45° C. | −ve |
| Catalase | +ve |
| Oxidase | −ve |
| Fermentative | No change | in Glucose OF

A cell wall and fatty acid analysis provided the following information.

Mycolic acids are present.

The cell wall diamino acid is mesoDAP.

The fatty acid profile shows that the major acids present are straight chain saturated and unsaturated acids together with a small amount of a 10-methyl branched acid i.e. tuberculostearic acid.

The enzymic activity can be produced by culturing *R. rhodochroits* on ROX or $NH_4Cl$ as a nitrogen source. To obtain the enzymic activity the cells can be disrupted in any conventional way. Conveniently a cell free extract is made. The extract may then be fractionated by ultracentrifugation and the pellet taken to provide active membrane fraction.

Alternatively the supernatant from ultracentrifugation provides active soluble protein. The soluble protein may be partially purified using anion exchange chromatography and eluted with a linear salt gradient from 0–2 M sodium chloride. The protein elutes as a single peak at approximately 350 mM sodium chloride.

The enzymic activity obtained as cell extract requires the presence of dithiothreitol (DTT) for RDX degrading enzymic activity.

Instead of the precise starting organism deposited, a mutant thereof, eg derived by gamma-ray irradiation or the use of a chemical mutant, induction by culture on another medium etc. or a transconjugant thereof with another bacterium or an artificially produced variant can be used. The ability of any such organism to give the enzymic activity can be readily determined by the skilled person.

The ability of the novel enzymic activity to catalyse the removal of nitrite from RDX allows the enzymic activity to be used in the detection of RDX. According to a further aspect of the invention therefore, there is provided a method of detecting the presence of RDX in a sample which comprises exposing the sample to the RDX-degrading enzymic activity and detecting any nitrite liberated from said sample. Conveniently such detection would be by means of a colorimetric method as is well known is the art.

The removal of nitrite from RDX may create an unstable intermediate which then spontaneously degrades to give a range of smaller molecules including formaldehyde and ammonia. In a further aspect of the present invention therfore there is provided a method of detecting the presence of RDX in a sample which comprises exposing the sample to the RDX degrading enzymic activity and detecting any formaldehyde produced. Such detection could again be by means of a colorimetric method as known in the art.

In a further aspect, the present invention also provides a biosensor for the detection of RDX in a sample which comprises means for contacting the sample with the RDX degrading enzymic activity and means for detecting occurrence of a reaction, catalysed by the enzymic activity, of RDX when RDX is present in the sample. Alternatively in a further aspect there is provided a biosensor for the detection of RDX in a sample which comprises means of inoculating the sample with a culture of the bacterial isolate *Rhodococcus rhodochrous* 11Y and maintaining the sample under conditions appropriate for degradation of the contaminent by the isolate and means of detecting the occurrence of a reaction, catalysed by the isolate, of RDX when RDX is present in the sample. The means for detecting the occurrence of a reaction may conveniently comprise a colorimetric transducer. Such sensors can be used as the basis for highly portable detectors for analysing the extent of contamination of the RDX pollutant within the environment.

A further aspect of this present invention is the provision of a method for the bioremdial treatment of an environment contaminated with RDX, which method comprises the steps of adding to the contaminated environment a quantity of cell extract containing the enzymic activity and maintaining the mixture under conditions appropriate for degradation of RDX by the enzymic activity such that the RDX present in the material is consumed.

The material consumed may be, for example, a waste stream of material containing RDX originating from the destruction of an explosives charge containing RDX or a sample of RDX-contaminated earth of other material. In the former case bioremdial treatment may be conveniently carried out in a reactor vessel, whereas in the latter instance the enzymic activity may be introduced directly into the material. Other appropriate methods of effecting treatment will be readily apparent to those skilled in the art.

According to a yet further aspect of the present invention, the ability of the enzymic activity to degrade RDX as described above provides an alternative method for the bioremedial treatment of a RDX-contaminated environment. This method comprises the step of inoculating the environment with a sample of the bacterial isolate of *Rhodococclis rhodochious* designated 11Y and allowing the isolate to consume the RDX present in the environment. The environment may be, for example, a waste stream of material containing RDX or a sample of RDX-contaminated earth or other material. In the former case bioremedial treatment may be conveniently carried out in a reactor vessel, whereas in the latter instance the isolate may be introduced directly into the environment by inoculating the contaminated soil with it. Other appropriate methods of effecting treatment will be readily apparent to those skilled in the art.

BRIEF DESCRIPTION OF THE DRAWINGS

The invention will now be further described by way of example only with reference to the following drawings of which.

EXAMPLE 1

Figure 1:
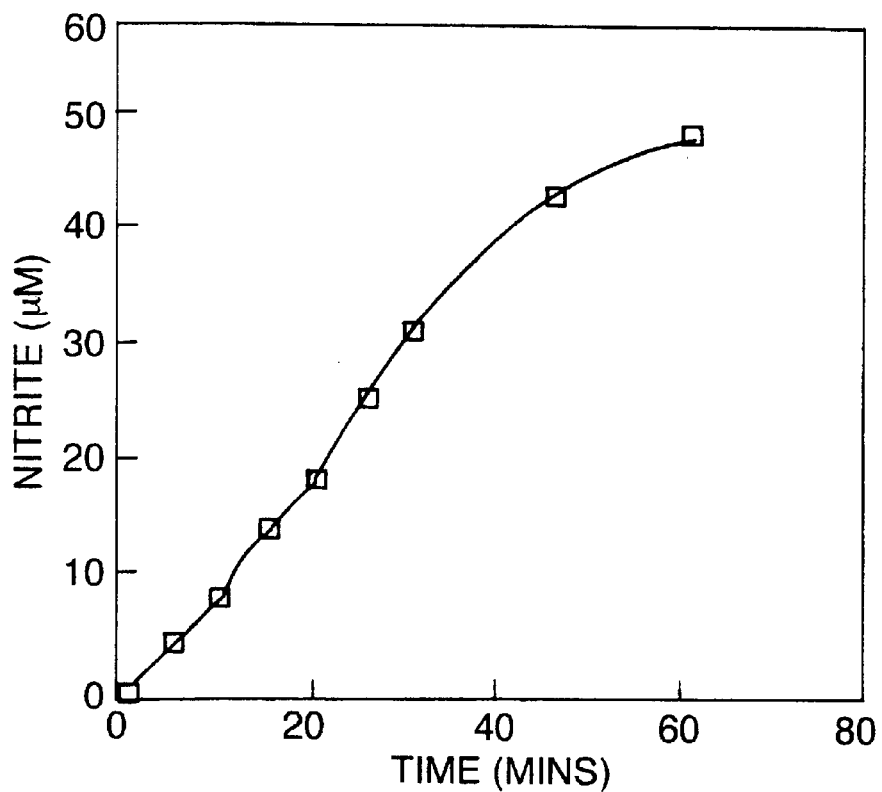
FIG. 1 shows the nitrite produced during the incubation of cell extract from *Rhodococcus Rhodochrous* 11Y with RDX.

1. Preparation of the Enzyme Activity from the Bacterial Strain *Rhodococcus Rhodochrous* 11Y.

*Rhodococcus rhodochrous* 11Y was isolated using techniques standard in the art, from samples collected from a natural source by enrichment with RDX as the nitrogen source.

*R. rhodochrous* 11Y was grown in 1 litre of defined media consisting of 2.17 g/l $Na_2HPO_4$ and 1.325 g/l $KH_2PO_4$, pH 7.0, containing 0.4% glucose (w/v), trace elements (as described by Pfennig and Lippert, Arch. Microbiology, 1966, 55, 726–739.) and either 1 mM RDX or 6 mM $NH_4Cl$. Flasks were incubated at 180 r.p.m in a shaking incubator at 30° C.

Cell free extracts were obtained from cells grown in the above manner. Cells were pelleted by spinning at 10,000g for 15 min at 4° C. in a Sorval RC-5C centrifuge fitted with a GS-3 rotor. These cells were resuspended in 2 ml of 50 mM Tricine buffer (pH 8.0), per gram wet cell weight. Cells were disrupted by sonication in an MSE Soniprep (Fisons, Instruments, FSA Ltd.) using 6×12 µm bursts of 15 seconds, alternated with 30 seconds of cooling in melted ice. Cell debris and unbroken cells were removed by centrifugation at 13,000g for 1 min at 4° C. in a microcentrifuge (Sigma). This supernatant was used as cell free extract. The membrane fraction was obtained from the cell free extract by ultracentrifugation at 109,000 g for 1 hour at 4° C. (Beckman Optima TLX Ultracentrifuge TLA 45 rotor), the pellet was washed and resuspended in 50 mnM Tricine buffer (pH 8.0) to a concentration of 2 mg/ml protein.

2. Chemicals

RDX was of the highest purity and other chemicals were of analytical grade, and unless stated otherwise, were obtained from BDH Ltd. (Poole, UK.), Sigma Chemical Company Ltd. (Poole, UK.) or Aldrich (Gillingham, UK).

3. Assays

RDX Degradation

RDX degradation was determined by monitoring the disappearance of RDX by HPLC in 50 mM Tricine(pH 8.0), containing RDX (50 µM, final concentration), 5 mM DTT and 40 µl cell free extract or membrane fraction in a final volume of 1 ml.

Alternatively, RDX degradation was followed by monitoring the release of nitrite using Griess reagent (Rosenblatt, Burrows, Mitchell and Partner. 1991: "Organic Explosives and Related Compounds" in the Handbook of Environmental Chemistry 3 (G), edited by O. Hutzinger, Springer-Veriag). The assay was carried out as described above. Sulphanilic acid (0.6 mM, final concentration) was added and left to stand for 15 min, N-1-naphthylethylenediamine (0.4 mM final concentration) was then added and after 5 min the colour which developed was measured spectrophotometrically at 540 nm.

Protein

Protein was routinely assayed by the Coomassie dye-binding method of Bradford (Anal. Biochem. (1976) 72, 248–254) using commercially available reagent and Bovine Serum Albumin standard (Pierce Ltd.—obtained through Life Science Labs Ltd., Luton). An aliquot (20 μl) of sample containing 0.2–1 mg protein/ml was added to 1 ml of reagent and the reaction allowed to develop for 5 min at room temperature prior to reading the absorbance at 595 nm against a blank of buffer (20 μl) plus reagent (1 ml). Comparison to a standard curve of standard balues (0–1 mg/ml) allowed calculation of the protein concentration in the sample.

4. Results

RDX—Degradation

Crude extract was incubated at 30° C. with 50 mM Tricine containing 50μM RDX and 5 mM DTT over a range of times from 0 to 60 min. The concentration of RDX was determined by using HPLC. The concentration of RDX was seen to decrease.

Membrane fraction was incubated at 30° C. with 50 mM Tricine containing 50 μm RDX and 5 mM DTT over a range of times from 0 to 60 min. The concentration of RDX was detected by using HPLC. The concentration of RDX was seen to decrease with elapsed time.

Nitrite Production

Crude extract was incubated at 30° C. with 50 mM Tricine containing 50 μM RDX and 5 mM DTT over a range of times from 0 to 60 min. The concentration of nitrite was then measured using Griess reagent. The concentration of nitrite was seen to increase as shown in FIG. 1.

Addition of any one of the co-factors NADH, NADPH, PES or FAD did not affect the rate of nitrite production, indicating depletable co-factor independent enzymic activity.

Membrane fraction incubated with 50 μM RDX at 30° C. also produced nitrite. Solubilisation of this activity was possible with 5% triton.

EXAMPLE 2

Cells of *R. rhodochrous* strain 11Y were grown in a medium consisting of 2.17 g/l $Na_2HPO_4$ and 1.325 g/l $KH_2PO_4$, pH 7.0, with 0.4% (w/v) glucose, 6 mM nitrogen atoms and trace elements (Pfennig & Lippert, supra). The cultures were incubated at 30° on a rotary shaker at 170 r.p.m.

Whole cells of 11Y were harvested by centrifugation of late exponential phase cultures at 7000 g for 10 minutes in a Sorvall RC5C centrifuge using a GS3 rotor. The cells were washed and suspended in 50 mM Tricine pH 8.0 to a concentration of 0.5 g/ml wet weight of cells.

The degradation of RDX in whole cell incubations of 11Y was assayed in 50 mM Tricine pH 8.0 containing RDX (300 μM final concentration) and 10 μl of whole cells in a final volume of 1 ml. The disappearance of RDX was monitored using thin layer chromatography (TLC) with detection using Griess reagent (Rosenblatt et al, supra). Alternatively the production of formaldehyde was monitored using the standard Hantzch spectrophotometric assay; 500 μl of sample was mixed with 500 μl of formaldehyde reagent (20 mM acetylacetone, 2 mM ammonium acetate and 50 mM acetic acid) (Nash, 1953, Biochemical Journal, Vol. 55, p416). The sample was then incubated at 58° C. for 10 minutes and the yellow colour formation measured at 418 nm using a diode array spectrophotometer. Known concentrations of formaldehyde (from 1 to 500 μM) were used to construct a calibration curve.

Figure 2:
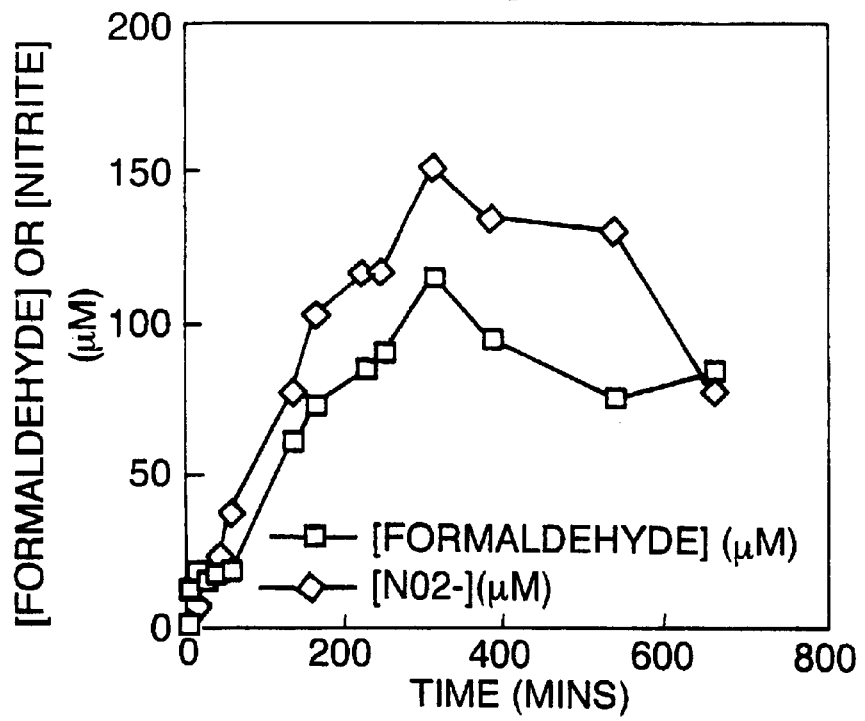
FIG. 2 shows the nitrite and formaldehyde produced during whole cell incubation of RDX with cells of *Rhodococcus Rhodochrous* 11Y.

The whole cell samples were incubated at 30° C. over a 12 hour period. The concentration of nitrite was seen to increase as shown in FIG. 2. FIG. 2 also shows that the concentration of formaldehyde also increased.

Whole cells were disrupted with a French Pressure Cell Press using the minicell at a pressure of 11,000 p.s.i. Cell debris and unbroken cells were removed by centrifugation at 13,000 r.p.m. for 1 minute at 4° C. in a microcentrifuge, the supernatant being used as crude cell extract.

RDX degrading and nitrite producing activity of the crude extract were assayed as follows; assays were performed in 50 mM Tricine buffer pH 8.0 containing RDX (50 μM final concentration), 5 mM DTT and 40 μl crude extract in a final volume of 1 ml. RDX degradation was determined by monitoring the disappearance of RDX by TLC with detection using Griess reagent. To measure the nitrite produced, proteins were precipitated by the addition of 2 Ml glacial acetic acid and then removed by centrifugation in a microcentrifuge (5 minutes, 13,000 r.p.m.). The standard Griess reaction for nitrite was performed. RDX degradation and concomitant nitrite production were observed.

Subcellular fractionation was achieved by ultracentrifugation of the crude extract at 109,000g for 1 hour at 4° C. (Beckman Optima TLX Ultracentrifuge TLA 45 rotor), the supernatant representing the soluble proteins and the pellet the membrane fraction. The pellet was washed and resuspended in 50 mM Tricine buffer pH 8.0 to a concentration of 2 mg/ml protein prior to activity studies.

RDX degrading ability was observed in both fractions with the majority being in the membrane fraction.

The RDX degrading enzymic activity in the soluble protein was partially purified by a Q-sepharose column using 50 mM Tris buffer pH 8.5 and a salt gradient of 0–2 M NaCl. The protein eluted as a single peak at around 350 mM sodium chloride. The partially purified protein was seen to be heat stable and was denatured in 6 M urea but refolded when diluted to 2 M urea.

EXAMPLE 3

1. Growth of *R. Rhodochrous* and Partial Purification of the Enzyme

16 L of *R. Rhodochrous* 11Y was cultured in 20 mM $KH_2PO_4$, 0.4% glucose (w/w), 2 ml of trace elements (Pfennig & Lippert, supra) and 1 mM RDX as the sole nitrogen source at 30° C. The cells were grown in 2 L flasks and were harvested by centrifugation once they had reached stationary growth phase in a Sorvall RC5C centrifuge using a GS3 rotor at 10,000 g for 15 minutes at 4° C. The cell pellet (57 g wet weight of cells) was resuspended in 120 ml of 50 mM Tris pH 8.0. The suspension was homogenised using a French pressure cell at 35,000 p.s.i. (three passes) followed by centrifugation (Sorvall RC5C centrifige using a SS-34 rotor at 30,000 g for 30 minutes at 4° C.) to pellet any cellular debris. The supernatant was removed and centrifuged again (Beckman XL-90 ultracentrifuge using a Ti-70 rotor at 25,000g for 2 hours at 4° C.) to pellet the bacterial membranes. Both supernatants and pellets were found to possess the ability to degrade RDX with the liberation of nitrite as determined by the Griess assay. The supernatant from the high speed centrifugation step was used for further purification.

The pH of the supernatant sample was reduced to 3.5 with glacial acetic acid and the sample incubated on ice for 30 minutes. It was found that ~60% of the protein from the high speed supernatant aggregated and was removed by further centrifugation (Sorvall RC5C centrifuge using a SS-34 rotor at 30,000 g for 30 minutes at 4° C.). The pH of the supernatant was then shifted to 8.0 using 1 M sodium hydroxide and the extract assayed for RDX linked nitrite release as described in example 1. It was found that the majority of the activity remained soluble after treatment with glacial acetic acid (~75%). This sample was used in all subsequent assays.

2. Substrate Requirements

Figure 3:
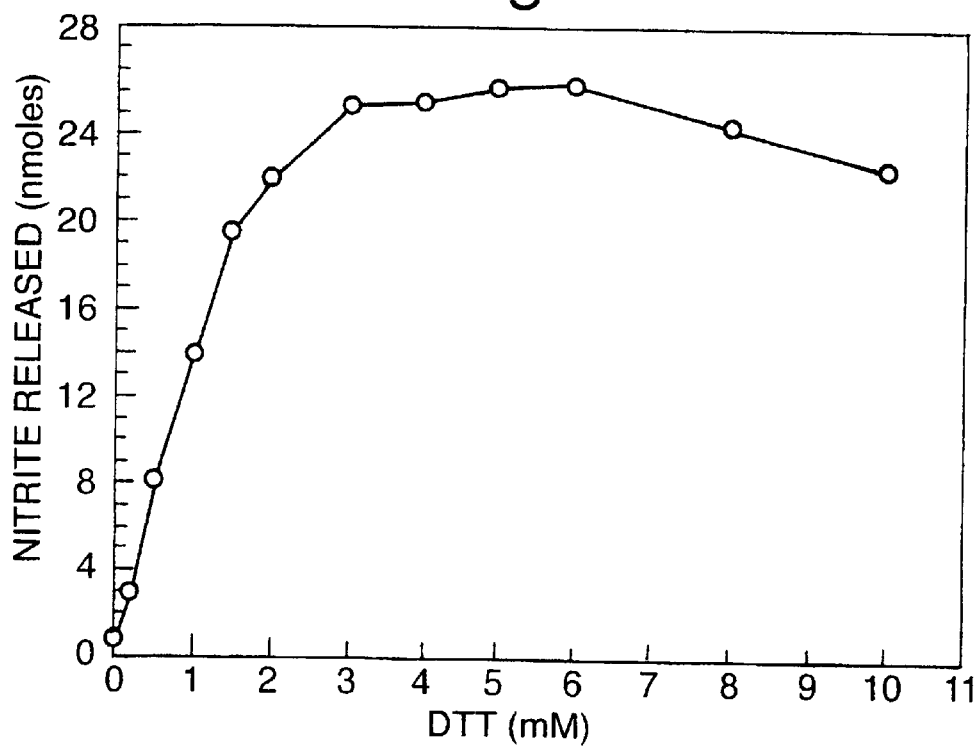
FIG. 3 shows the variation of nitrite produced in incubations of partially purified extract from *Rhodococcus Rhodochrous* 11Y with concentration of dithiothreitol.

Using the partially purified protein the requirements for co-factors was investigated. There was found to be no need for a cofactor such as NADPH or NADH. The dependence of RDX degradation with the concentration of diothiothreitol (DTT) was assayed as follows; 26 µg of partially purified protein was incubated in the presence of 4M urea, 0.3 mM RDX, 50 mM Tricine pH 8.5 at 37° C. for 10 minutes. The concentration of DTT was varied and the final volume maintained at 200 µl. The amount of nitrite released was measured using a spectrophometric assay as described in example 1. The amount of nitrite released with concentration of DTT is shown in FIG. 3. This shows a preference for the presence of DTT with ~3 mM of DTT being required to achieve maximum activity. DTT is used to maintain a reducing environment once the cells have been disrupted.

Solubility and Stability

Concentration the partially purified enzyme solution using an Amicon ultrafiltration unit (3 kDa cut of membrane, 70 p.s.i. at 4° C.) lead to the protein aggregating and a reduction of activity. It was found that the aggregated protein could be resolubilised in 8 M urea, 5 mM DTT and 50 mM Tris pH 8.0 and activity restored.

Figure 4:
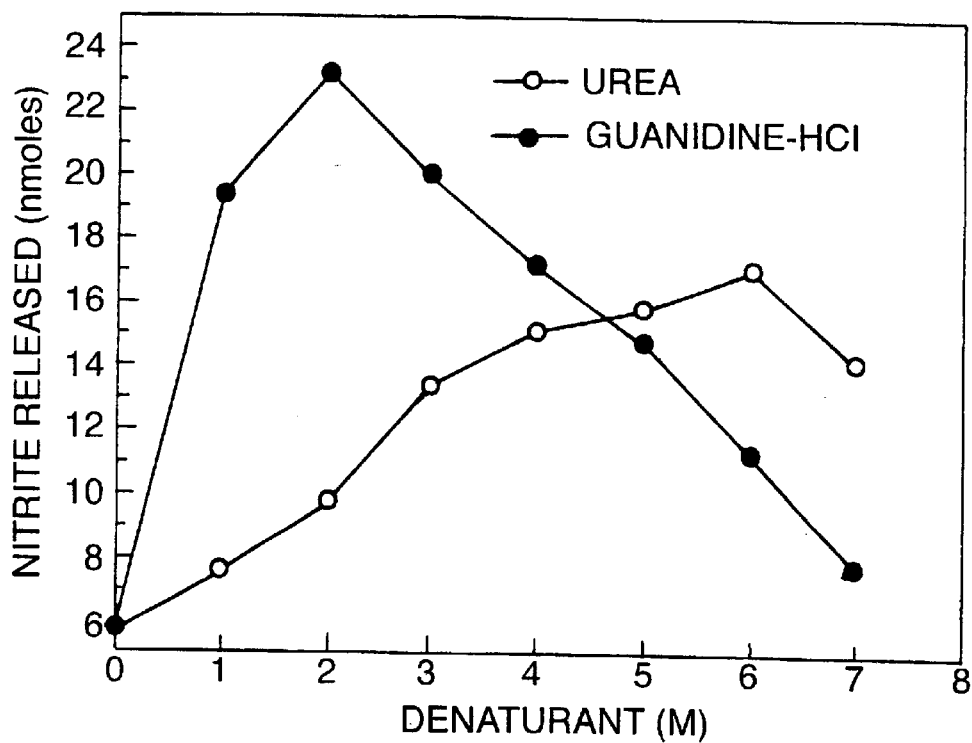
FIG. 4 shows the nitrite released from incubation of RDX with partially purified extract with varying concentration of denaturants.

The stability of the enzymic activity in the presence of strong denaturing agents was measured by assaying for the release of nitrite from RDX in the presence of the protein sample with urea or guanidine hydrochloride. The assay conditions were 50 mM Tricine pH 8.5, 0.3 mM RDX, 5 mnM DTT at 37° C. for 10 minutes with 26 Mg of protein the release of nitrite being measured by the spetrophotometric assay as described in example 1. The dependence of RDX activity on the concentration of denaturant is shown in FIG. 4.

It can be seen that the enzyme shows an unusually high stability to the presence of high concentrations of denaturants. The difference in activity observed with urea, which predominantly acts by disrupting hydrogen bonds and hydrophobic interactions within proteins, and guanidium hydrochloride, which predominantly disrupts ionic interactions and to a lesser extent hydrophobic interaction, suggests that ionic interactions may play a greater part in the stability of the enzymic activity.

As the RDX degrading activity was enhanced by the presence of urea all subsequent assays were carried out with 4 M urea present.

Figure 5:
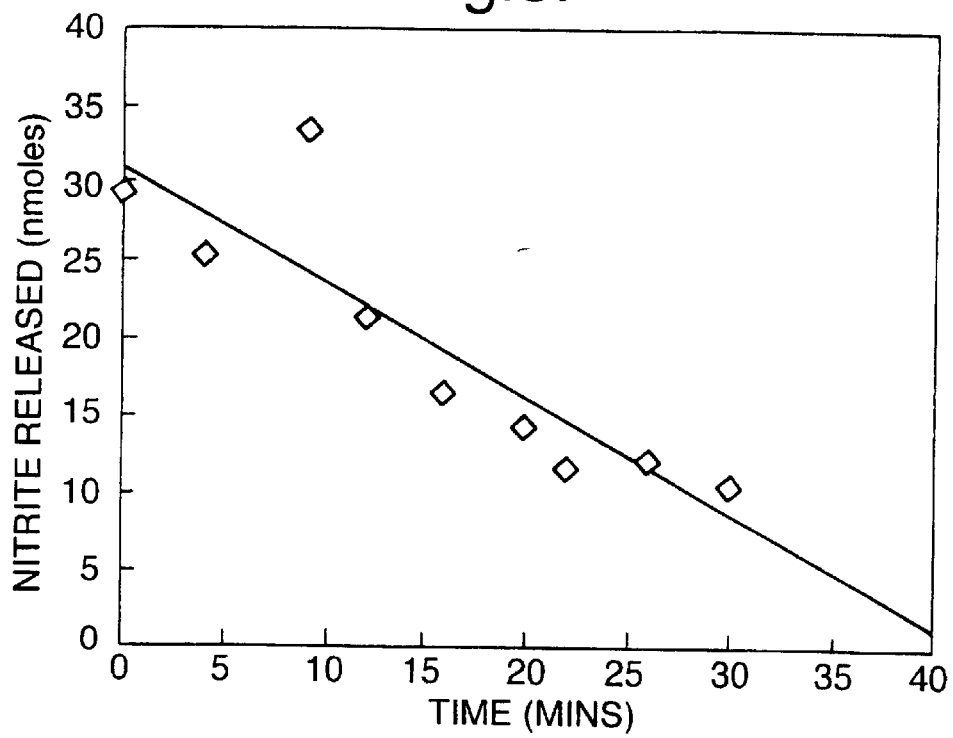
FIG. 5 shows nitrite released against time of boiling for incubations of heat treated partially purified extract with RDX.

To determine the heat stability of the enzymic activity the partially purified protein sample was heated at 100° C. and samples taken at various intervals and assayed for 10 minutes with 20 µl of boiled sample, 50 mM Tricine pH 8.5, 4 M urea, 5 mM DTT and 0.3 mM RDX at 37° C. The release of nitrite was measured spectrophotometrically and the results are shown in FIG. 5.

It can be seen that the enzymic activity is relatively stable to heat, losing only ~20% activity after 10 minutes at 100° C.

4. pH Profile

Figure 6:
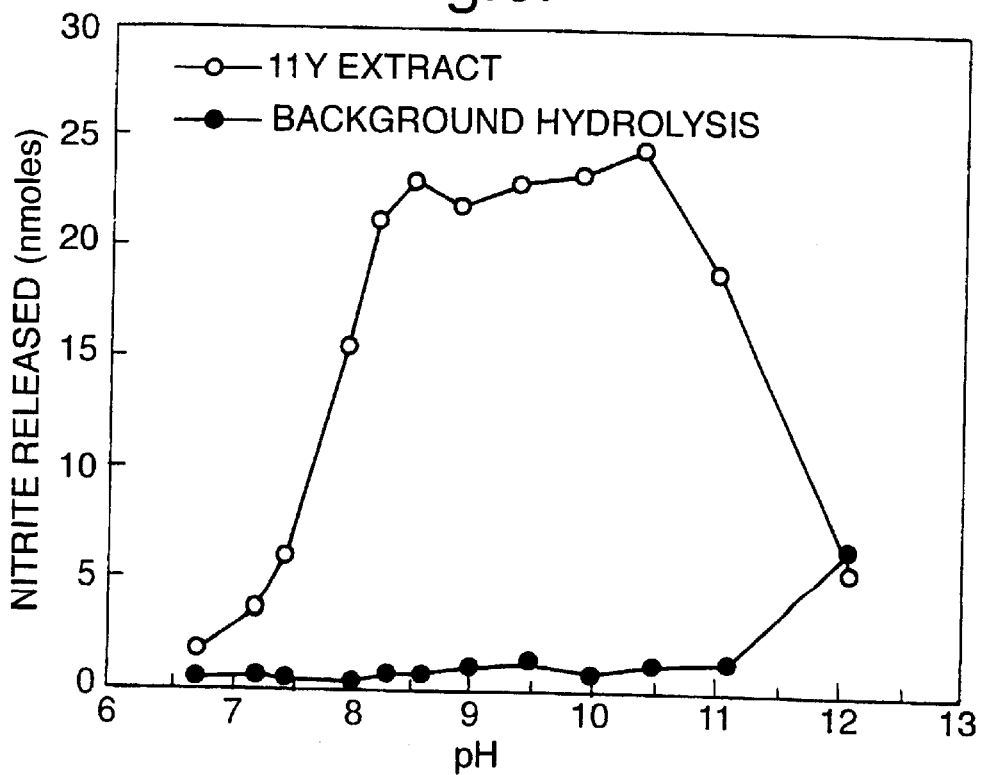
FIG. 6 shows the pH profile of release of nitrite from incubations of partially purified extract with RDX and the spontaneous hydrolysis of RDX.

The pH profile of the partially purified extract was investigated. The assay conditions were 50 mM of the appropriate buffer, 4 M urea, 0.3 mM RDX and 5 mnM DTT. The samples were incubated at 37° C. for 10 minutes with 26 µg of partially purified protein. The alkaline hydrolysis of 0.3 mM of RDX was also measured under identical conditions and the results are shown in FIG. 6. It can be seen that the enzymic activity significantly increases the release of nitrite from RDX compared to spontaneous breakdown over the pH range.

5. Nitrite and Formaldehyde Production

The production of nitrite and formaldehyde from the enzymatic breakdown of RDX was assayed in 50 mM Tricine pH 8.5, 4 M urea, 0.15 mM RDX and 5 mM DTT at 37° C. with 26 µg of partially purified extract and the amount of nitrite liberated and formaldehyde produced measured over time using the standard spectrophotometric assays as described in example 1.

Figure 7:
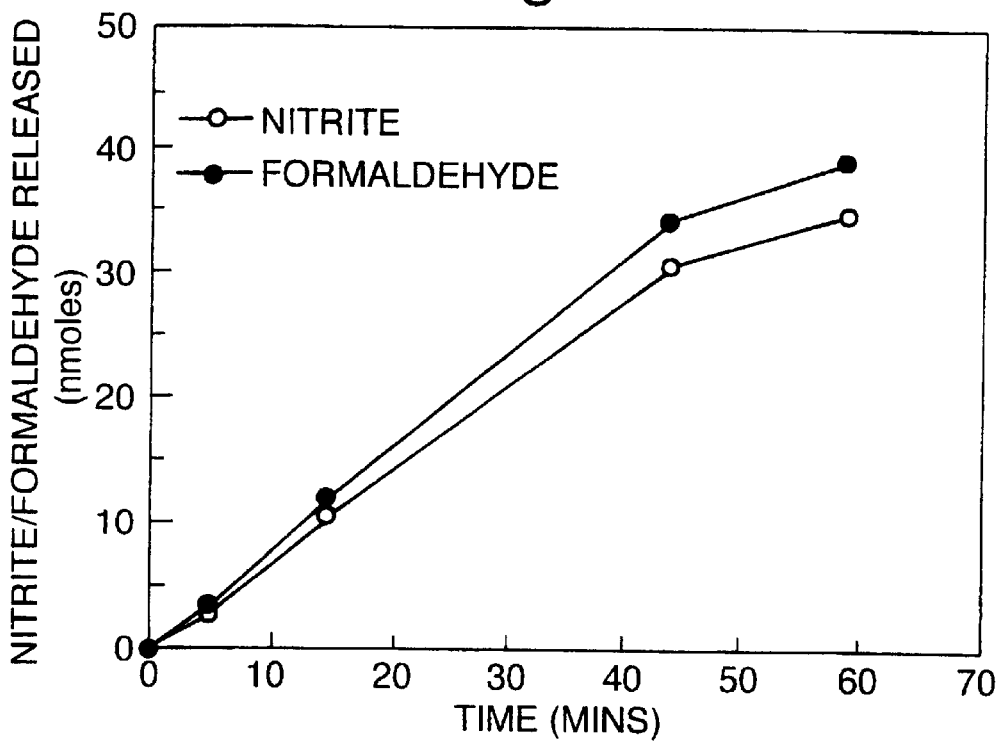
FIG. 7 shows the nitrite and formaldehyde liberated during the course of incubations of partially purified extract with RDX.

The results are shown in FIG. 7. The amounts of formaldehyde and nitrite released from RDX were similar, suggesting that the mechanism of enzymatic breakdown of RDX may be similar to that proposed for the alkaline hydrolysis of RDX (Croce and Okamoto, 1978, Journal of Organic Chemistry, Vol. 44, pp 2100–2103; Heilmann et al, 1996, Environmental Science Technology, Vol. 30, No. 5, pp 1485–1492) where removal of a nitrite group from RDX forms an unstable intermediate which spontaneously degrades to give a range of smaller molecules including formaldehyde.

6. Substrate Specificity

Figure 8:
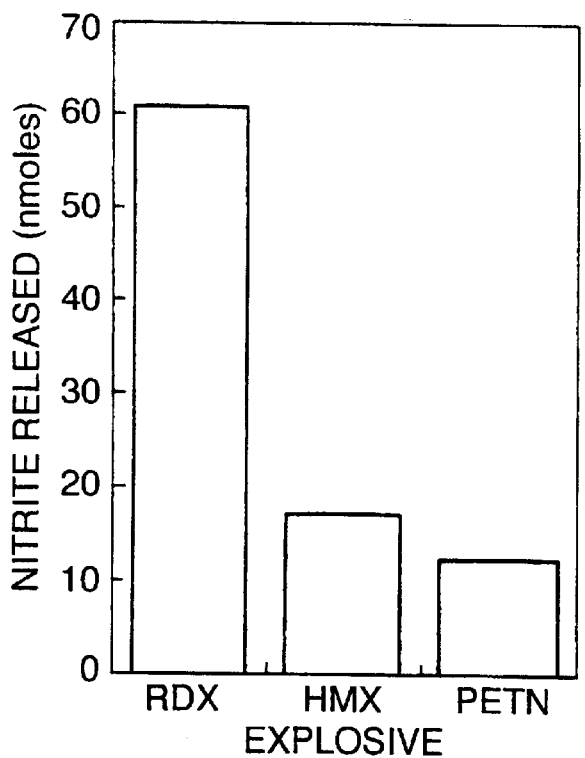
FIG. 8 shows the nitrite liberated from incubations of partially purified extract with various nitrite containing explosives.

The substrate specificity was investigated by testing if the enzymic activity degraded HMX or PETN, both nitrite containing explosives. The assays were carried out in 50 mM Tricine, 4 M urea, 0.3 mM of the appropriate explosive and 5 mM DTT at 37° C. for 20 minutes with 26 µg of partially purified extract and the results compared with RDX. The results are shown in FIG. 8. It can be seen that the enzymic activity was active against all the explosives tested but there was a clear preference (i.e. greater activity) for RDX.

What is claimed is:

1. A biologically pure culture of *Rhodoccous rhodochrous* NCIMB 40820, and mutants thereof having all of the identifying charateristics of said strain, wherein said strain is capable of producing a protein having enzymic activity which degrades hexahydro-1,3,5-trinitro-1,3,5-triazine (RDX).

2. An RDX degrading protein having enzymic activity produced by the culture of claim 1, wherein said protein catalyses the release of nitrite during the degradation of hexahydro-1,3,5-trinitro-1,3,5-triazine (RDX).

3. A method for the production of a RDX-degrading protein having enzymic activity comprising:
   1) culturing the *Rhodococcus rhodochrous* strain NCIMB 40820 of claim 1,
   2) disrupting the cells; and
   3) extracting the protein having enzymic activity from the disrupted cells.

4. A method of detecting hexahydro-1,3,5-trinitro-1,3,5-triazine (RDX) in a sample, comprising exposing the sample to the RDX-degrading protein having enzymic activity of claim 2 and detecting any nitrite which is produced from said sample.

5. A method according to claim 4 where the nitrite is detected colorimetrically.

6. A method of detecting hexahydro-1,3,5-trinitro-1,3,5-triazine (RDX) in a sample, comprising exposing the sample to the RDX degrading protein having enzymic activity of claim 2 and detecting any formaldehyde which is produced from said sample.

7. A method according to claim 6 where the formaldehyde is detected colorimetrically.

8. A method according to any one of claims 4 to 7 wherein the method includes the step of addinge dithiothreitol to the sample.

9. A biosensor for the detection of hexahydro-1,3,5-trinitro-1,3,5-triazine (RDX) in a sample which comprises means for contacting the sample with the RDX-degrading protein having enzymic activity of claim 2 and maintaining the sample under conditions appropriate for degradation of the RDX by said enzymic activity and further comprises means for detecting the occurrence of a reaction, catalysed by said enzymic activity, of the hexahydro-1,3,5-trinitro-1,3,5-triazine (RDX) present in the sample.

10. A biosensor for the detection of hexahydro-1,3,5-trintro-1,3,5-triazine (RDX) in a sample which comprises means for innoculating the sample with the culture of claim 1 and maintaining the sample under conditions appropriate for degradation of the RDX by the culture, and further comprises means for detecting the occurrence of a reation, catalysed by the culture during degradation of RDX present in the sample.

11. A biosensor according to claim 9 or claim 10 wherein the means for detecting the occurrence of a reaction is a colorimetric change.

12. A method for the bioremedial treatment of an environment contaminated with hexahydro-1,3,5-trinitro-1,3,5-triazine (RDX) comprising the steps of 1) adding to the environment an effective amount of the RDX degrading protein having enzymic activity of claim 2 to form a mixture and 2) maintaining the mixture under conditions appropriate for degradation of the contaminant by the enzymic activity to allow the hexahydro-1,3,5-trinitro-1,3,5-triazine (RDX) present in the environment to be consumed.

13. A method according to claim 12 wherein the step of maintaining the mixture under conditions appropriate for degradation of the contaminant by the enzymic activity includes adding dithiothreitol to the mixture.

* * * * *